(12) United States Patent
Hastings et al.

(10) Patent No.: US 9,579,356 B2
(45) Date of Patent: Feb. 28, 2017

(54) DIETARY SUPPLEMENTS FOR REDUCING CHOLESTEROL LEVELS

(75) Inventors: Carl W. Hastings, Wildwood, MO (US); David J. Barnes, O'Fallon, MO (US); Scott C. Kubel, St. Louis, MO (US)

(73) Assignee: RELIV INTERNATIONAL INC., Chesterfield, MI (US)

( * ) Notice: Subject to any disclaimer, the term of this patent is extended or adjusted under 35 U.S.C. 154(b) by 1078 days.

(21) Appl. No.: 11/339,135

(22) Filed: Jan. 25, 2006

(65) Prior Publication Data
US 2007/0172468 A1    Jul. 26, 2007

(51) Int. Cl.
| | | |
|---|---|---|
| A61K 36/537 | (2006.01) | |
| A61K 36/48 | (2006.01) | |
| A61K 31/045 | (2006.01) | |
| A61K 31/555 | (2006.01) | |
| A61K 36/28 | (2006.01) | |
| A61K 36/68 | (2006.01) | |
| A61K 36/899 | (2006.01) | |

(52) U.S. Cl.
CPC ............ *A61K 36/48* (2013.01); *A23L 33/105* (2016.08); *A23L 33/11* (2016.08); *A61K 31/045* (2013.01); *A61K 31/555* (2013.01); *A61K 36/28* (2013.01); *A61K 36/537* (2013.01); *A61K 36/68* (2013.01); *A61K 36/899* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,906,470 A * | 3/1990 | Liu | 424/745 |
| 5,294,606 A | 3/1994 | Hastings | |
| 5,458,893 A * | 10/1995 | Smith | 426/18 |
| 5,567,424 A | 10/1996 | Hastings | |
| 5,626,849 A | 5/1997 | Hastings et al. | |
| 6,224,871 B1 | 5/2001 | Hastings et al. | |
| 6,299,910 B1 | 10/2001 | Xu et al. | |
| 6,368,617 B1 | 4/2002 | Hastings et al. | |
| 6,500,469 B1 | 12/2002 | Preuss et al. | |
| 6,589,572 B2 * | 7/2003 | Hong et al. | 424/728 |
| 6,642,277 B1 * | 11/2003 | Howard et al. | 514/783 |
| 2001/0034338 A1 * | 10/2001 | Sorkin, Jr. | 514/171 |
| 2002/0103139 A1 * | 8/2002 | Weisspapir et al. | 514/26 |
| 2004/0034241 A1 * | 2/2004 | Empie et al. | 552/540 |
| 2005/0100619 A1 * | 5/2005 | Chen et al. | 424/745 |
| 2005/0163872 A1 * | 7/2005 | Khare | 424/748 |
| 2006/0013861 A1 * | 1/2006 | Guthrie | 424/439 |

OTHER PUBLICATIONS

Ballantyne, Rationale for targeting multiple lipid pathways for optimal cardiovascular risk reduction, 2005, Am J Cardiol, 96, 14K-19K.*
"High Blood Cholesterol and Other Lipids—Statistics," *American Heart Association*, (2004).
Anderson et al., "Cholesterol-Lowering Effects of Psyllium Intake Adjunctive to Diet Therapy in Men and Women with Hypercholesterolemia: Meta-Analysis of 8 Controlled Trials," *Am. J. Clin. Nutr.*, 71: 472-479 (2000) (Abstract).
Anderson et al., "Hypocholesterolemic Effects of Oat and Bean Products," *Am. J. Clin. Nutr.*, 48 (3 Suppl): 749-753 (1988) (Abstract).
Anderson et al., "Hypocholesterolemic Effects of Oat-Bran or Bean Intake for Hypercholesterolemic Men," *Am. J. Clin. Nutr.*, 40 (6): 1146-1155 (1984) (Abstract).
Anderson et al., "Lipid Responses of Hypercholesterolemic Men to Oat-Bran and Wheat-Bran Intake," *Am. J. Clin. Nutr.*, 54 (4): 678-683 (1991) (Abstract).
Anderson et al., "Long-term Cholesterol-Lowering Effects of Psyllium as an Adjunct to Diet Therapy in the Treatment of Hypercholesterolemia," *Am. J. Clin. Nutr.*, 71 (6): 1433-1438 (2000).
Anderson et al., "National Vital Statistics Reports, Deaths: Leading Cases for 2002," *CDC*, 53 (17): 1-92 (2005).
Anderson et al., "Oat-Bran Cereal Lowers Serum Total and LDL Cholesterol in Hypercholesterolemic Men," *Am. J. Clin. Nutr.*, 52 (3): 495-499 (1990) (Abstract).
Anderson, "Chromium Metabolism and itsRole in Disease Processes in Man," *Clin. Physiol. Biochem.*, 4 (1): 31-41 (1986) (Abstract).
Andriambeloson et al., "Natural Dietary Polyphenolic Compounds Cause Endothelium-Dependant Vasorelaxation in Rat Thoracic Aorta," *J. Nutr.*, 128 (12): 2324-2333 (1998).
Arichi et al., "Effects of Stilbene Components of the Roots of Polygonum Cuspidatum on Lipid Metabolism," *Chem. Pharm. Bull.*, 30: 1766-1770 (1982) (Abstract).
Arruzazabala et al., "Effect of Policosanol on Platelet Aggregation in Type II Hypercholesterolemic Patients," *Int. J. Tissue React.*, 20 (4): 119-124 (1998) (Abstract).
Arruzazabala et al., "Comparative Study of Policosanol, Aspirin and the Combination Therapy Policosanol-Aspirin on Platelet Aggregation in Healthy Volunteers," *Pharmacol. Res.*, 36 (4): 293-297 (1997) (Abstract).
Awad et al., "Effect of Phytosterols on Cholesterol Metabolism and MAP Kinase in MDA-MB231 Human Breast Cancer Cells," *J. Nutr. Biochem.*, 14 (2): 111-119 (2003) (Abstract).
Bays et al., "Pharmacotherapy for Dyslipidaemia-Current Therapies and Future Agents," *Expert Opin. Pharmacother.*, 4 (11): 1901-1938 (2003).
Bell et al., "Effect of Beta-Glucan from Oats and Yeast on Serum Lipids," *Crit. Rev. Food Sci. Nutr.*, 39 (2): 189-202 (1999).
Blardi et al., "Stimulation of Endogenous Adenosine Release by Oral Administration of Quercetin and Resveratrol in Man," *Drugs Exptl. Clin. Res.*, 25 (2-3): 105-110 (1999) (Abstract).
Caron et al., "Evaluation of the Antihyperlipidemic Properties of Dietary Supplements," *Pharmacotherapy*, 21 (4): 481-487 (2001).
Castelli et al., "Lipids and Risk of Coronary Heart Disease—The Framingham Study," *AEP*, 2 (1/2): 23-28 (1992).
Chen et al., "Meta-Analysis of Natural Therapies for Hyperlipidemia: Plant Sterols and Stanols Versus Policosanol," *Pharmacotherapy*, 25: 171-183 (2005).

(Continued)

*Primary Examiner* — Terry A McKelvey
*Assistant Examiner* — Catheryne Chen
(74) *Attorney, Agent, or Firm* — Marshall, Gerstein & Borun LLP

(57) ABSTRACT

The disclosure is generally directed to methods and compositions for reducing blood cholesterol levels, and more particularly to dietary supplements for reducing blood cholesterol levels. The dietary supplements for reducing cholesterol typically comprise at least one phytosterol source, at least one soluble fiber source, at least one guggulsterone source, and at least one policosanol source.

18 Claims, No Drawings

(56) References Cited

OTHER PUBLICATIONS

Chen et al., "Vasorelaxing Activity of Resveratrol and Quercetin in Isolated Rat Aorta," *Gen. Pharmacol.*, 27 (2): 363-366 (1996) (Abstract).
Chobanian et al., "Seventh Report of the Joint National Committee on Prevention, Detection, Evaluation, and Treatment of High Blood Pressure," *Hypertension*, 42: 1206-1252 (2003) (Abstract).
Cicero et al., "Effects of a New Soy/Beta-Sitosterol Supplement on Plasma Lipids in Moderately Hypercholesterolemic Subjects," *J. Am. Diet Assoc.*, 102 (12) : 1807-1811 (2002) (Abstract).
Cighetti et al., "Modulation of HMG-CoA Reductase Activity by Pantetheine/Pantethine," *Biochim. Biophys. Acta.*, 25: 389-393 (1988) (Abstract).
Cooper et al., "Structure and Biological Activity of Nitrogen and Oxygen Coordinated Nicotinic Acid Complexes of Chromium," *Inorganica Chim. Acta*, 91: 1-9 (1984).
Coronel et al., "Treatment of Hyperlipemia in Diabetic Patients on Dialysis with a Physiological Substance," *Am. J. Nephrol.*, 11 (1): 32-36 (1991) (Abstract).
Crawford et al., "Effects of Niacin-Bound Chromium Supplementation on Body Composition in Overweight African-American Women," *Diab. Obes. Metab.*, 1 (6): 331-337 (1999) (Abstract).
Davidson et al., "Long-Term Effects of Consuming Foods Containing Psyllium Seed Husk on Serum Lipids in Subjects with Hypercholesterolemia," *Am. J. Clin. Nutr.*, 67 (3): 367-376 (1998).
De Angelis, "The Influence of Statin Characteristics on Their Safety and Tolerability," *Int. J. Clin. Pract.*, 58: 945-955 (2004).
de Vegt et al., "Relation of Impaired Fasting and Postload Glucose with Incident Type 2 Diabetes in a Dutch Population: The Hoom Study," *JAMA*, 285: 2109-2113 (2001) (Abstract).
Detre et al., "Studies on Vascular Permeability in Hypertension: Action of Anthocyanosides," *Clin. Physiol. Biochem.*, 4 (2): 143-149 (1986) (Abstract).
Englisch et al., "Efficacy of Artichoke dry extract in patients with hypertipoproteinemia," *Arzneimittelforschung*, 50: 260-265 (2000).
"Executive Summary of the Third Report of the National Cholesterol Education Program (NCEP) Expert Panel on Detection, Evaluation, and Treatment of High Blood Cholesterol in Adults (Adult Treatment Panel III)," *JAMA*, 285 (19): 2486-2497 (2001).
Frankel et al., "Inhibition of Human LDL Oxidation by Resveratrol," *The Lancet*, 341: 1103-1104 (1993).
Gebhardt, "Inhibitibn of Cholesterol Biosynthesis in HepG2 Cells by Artichoke Extracts is Reinforced by Glucosidase Pretreatment," *Phytother. Res.*, 16: 368-372 (2002) (Abstract).
Grant et al., "Chromium and Exercise Training: Effect on Obese Women," *Med. Sci. Sports Exerc.*, 29: 992-998 (1997) (Abstract).
Heinemann et al., "Comparison of Intestinal Absorption of Cholesterol with Different Plant Sterols in Man," *Eur. J. Clin. Invest.*, 23: 827-831 (1993).
Hernandez et al., "Effect of Policosanol on Serum Lipids and Lipoproteins in Health Volunteers," *Current Therap. Res.*, 51: 568-575 (1992).
Howard et al., "PhYtochemicals and Cardiovascular Disease. A Statement for Healthcare Professionals from the American Heart Association," *Circulation*, 95: 2591-2593 (1997).
Jenkins et al., "A Dietary Portfolio Approach to Cholesterol Reduction: Combined Effects of Plant Sterols, Vegetable Proteins, and Viscous Fibers in Hypercholesterolemia," *Metabolism*, 51 (12): 1596-1604 (2002) (Abstract).
Kadar et al., "Influence of Anthocyanoside Treatment on the Cholesterol-Induced Atherosclerosis in the Rabbit," *Paroi Arterielle*, 5 (4): 187-205 (1979) (Abstract).
Katan et al., "Efficacy and Safety of Plant Stanols and Sterols in the Management of Blood Cholesterol Levels," *Mayo Clin. Proc.*, 78: 965-978 (2003) (Abstract).
Kelly et al., "Recent Trends in Use of Herbal and Other Natural Products," *Arch. Intern. Med.*, 165: 281-286 (2005) (Abstract).

Kerckhoffs et al., "Effects on the Human Serum Lipoprotein Profile of Beta-Glucan, Soy Protein and Isoflavones, Plant Sterols and Stanols, Garlic and Tocotrienols," *J. Nutr.*, 132: 2494-2505 (2002) (Abstract).
Lamarche et al., "Triglycerides and HDL-cholesterol as risk factors for ischemic heart disease. Results from the Quebec cardiovascular study," *Atherosclerosis*, 119: 235-245 (1996).
Maki et al., "Food Products Containing Free Tall Oil-Based Phytosterols and Oat Beta-Glucan Lower Serum Total and LDL Cholesterol in Hypercholesterolemic Adults," *J. Nutr.*, 133 (3): 808-813 (2003).
Malhotra et al., "The Effect of Various Fractions of Gum Guggul on Experimentally Produced Hypercholesteraemia in Chicks," *Indian J. Med. Res.*, 58 (3): 394-395 (1970).
Mas et al., "Effects of Policosanol in Patients with Type II Hypercholesterolemia and Additional Coronary Risk Factors," *Clin. Pharmaco. Ther.*, 65 (4): 439-447 (1999) (Abstract).
McCarty, "Policosanol Safely Down-Regulates HMG-CoA Reductase—Potential as a Component of the Esselstyn Regimen," *Med. Hypotheses*, 59 (3): 268-279 (2002).
McCarty, "Inhibition of Acetyl-CoA Carboxylase by Cystamine May Mediate and Hypotriglyceridemic Activity of Pantethine," *Med. Hypotheses*, 56 (3): 314-317 (2001) (Abstract).
Moghadasian et al., "Effects of Dietary Phytosterols on Cholesterol Metabolism and Atherosclerosis: Clinical and Experimental Evidence," *Am. J. Med.*, 107 (6): 588-594 (1999) (Abstract).
Naruta et al., "Hypolipidemic Effect of Pantothenic Acid Derivatives in Mice with Hypothalamic Obesity Induced by Aurothioglucose," *Exp. Toxicol. Pathol.*, 53 (5): 393-398 (2001) (Abstract).
Nigdikar et al., "Consumption of Red Wine Polyphenols Reduces the Susceptibility of Low-Density Lipoproteins to Oxidation In Vivo," *Amer. J. Clin. Nutr.*, 68 (2): 258-265 (1998) (Abstract).
Pace-Asciak et al., "The Red Wine Phenolics Trans-Resveratrol and Quercetin Block Human Platelet Aggregation and Eicosanoid Synthesis: Implications for Protection Against Coronary Heart Disease," *Clin. Chim. Acta*., 235 (2): 207-219 (1995) (Abstract).
Pittler et al., "Artichoke Leaf Extract for Treating Hypercholesterolaemia," *Cochrane Database Syst. Rev.*, CD003335 (3) (2002) (Abstract).
Preuss et al., "Chromium Update: Examining Recent Literature 1997-1998," *Curr. Opin. Clin. Nutr. Metab. Care*, 1 (6): 509-512 (1998) (Abstract).
Preuss et al., "Effects of Niacin-Bound Chromium and Grape Seed Proanthocyanidin Extract on the Lipid Profile of Hypercholesterolemic Subjects: A Pilot Study," *J. Med.*, 31 (5 & 6): 227-246 (2000).
Ridker et al., "Plasma Homocysteine Concentration, Statin Therapy, and the Risk of First Acute Coronary Events," *Circulation*, 105: 1776-1779 (2002) (Abstract).
Rotondo et al., "Red Wine, Asprin and Platelet Function," *Thromb. Haemost.*, 76: 818-819. (1996) (Abstract).
Roy et al., "Anti-Angiogenic Property of Edible Berries," *Free Rad. Res.*, 36 (9): 1023-1031 (2002) (Abstract).
Sato et al., "Myocardial Protection by Protykin, a Novel Extract of Trans-Resveratrol and Emodin," *Free Rad. Res.*, 32 (2): 135-144 (2000) (Abstract).
Selhub et al., "Serum Total Homocysteine Concentrations in the Third National Health and Nutrition Examination Survey (1991-1994): Population Reference Ranges and Contribution of Vitamin Status to High Serum Concentrations," *Ann. Intern. Med.*, 131 (5): 331-339 (1999).
Sempos et al., "Prevalence of High Blood Cholesterol Among US Adults. An Update Based on Guidelines from the Second Report of the National Cholesterol Education Program Adult Treatment Panel," *JAMA*, 269 (23): 3009-3014 (1993).
Singh et al., "Hypolipidemic and Antioxidant Effects of Commiphora Mukul as an Adjunct to Dietary Therapy in Patients with Hypercholesterolemia," *Cardiovasc. Drugs Ther.*, 8 (4): 659-664 (1994) (Abstract).
Spilburg et al., "Fat-Free Foods Supplemented with Soy Stanol-Lecithin Powder Reduce Cholesterol Absorption and LDL Cholesterol," *J. Am. Diet Assoc.*, 103 (5): 577-581 (2003) (Abstract).

(56) References Cited

OTHER PUBLICATIONS

Sun et al., "Study on Activating Blood and Eliminating Stasis of Guanxin Dansheng Capsule," *Zhong Yao Cai.*, 25: 119-121 (2002) (Abstract).

Szapary et al., "Guggulipid for the Treatment of Hypercholesterolemia: A Randomized Controlled Trial," *JAMA*, 290: 765-772 (2003) (Abstract).

Tang et al., "Systematic Review of Dietary Intervention Trials to Lower Blood Total Cholesterol in Free-Living Subjects," *BMJ*, 316: 1213-1220 (1998) (Abstract).

Thompson et al., "Herbs for Serum Cholesterol Reduction: A Systematic View," *J. Fam. Pract.*, 52: 468-478 (2003) (Abstract).

Urizar et al., "A Natural Product that Lowers Cholesterol as an Antagonist Ligand for FXR," *Science*, 31: 1703-1706 (2002) (Abstract).

Urizar et al., "Gugulipid: A Natural Cholesterol-Lowering Agent," *Annu. Rev. Nutr.*, 23: 303-313 (2003).

Walaszek et al., "d-Glucaric Acid Content of Various Fruits and Vegetables and Cholesterol-Lowering Effects of Dietary d-Glucarate in the Rat," *Nutr. Res.*, 16 (4): 673-681 (1996).

Walaszek et al., "Metabolism, Uptake, and Excretion of a d-Glucaric Acid Salt and Its Potential Use in Cancer Prevention," *Cancer Detect. Prev.*, 21 (2): 178-190 (1997) (Abstract).

Weststrate et al., "Plant Sterol-Enriched Margarines and Reduction of Plasma Total-and LDL-Cholesterol Concentrations in Normocholesterolaemic and Mildly Hypercholesterolaemic Subjects," *Eur. J. Clin. Nutr.*, 52 (5): 334-343 (1998) (Abstract).

Yokozawa et al., "Renal Responses to Magnesium Lithospermate B in Rats with Adenine-Induced Renal Failure," *Phytother. Res.*, 7: 235-239 (1993) (Abstract).

Yoshida et al., "Increased Myocardial Tolerance to Ischemia-Reperfusion Injury by Feeding Pigs with Coenzyme Q10," *Annals of the New York Academy of Sciences*, 793: 414-418 (1996) (Abstract).

Yoshimi et al., "Inhibition of Azoxymethane-Induced Rat Colon Carcinogenesis by Potassium Hydrogen d-Glucarate," *Int. J. Oncol.*, 16 (1): 43-48 (2000) (Abstract).

Zaragoza et al., "Estudio Comparativo de los Efectos Antiagregantes de los Antocianosidos y Otros Agentes," *Arch. Farmacol. Toxicol.*, 11 (3): 183-188 (1985) (English Summary).

Zhang et al., "Study on the Association of Lecithin Cholesterol Acyltransferase Gene Polymorphisms with the Lipid Metabolism in Coronary Atherosclerotic Heart Disease," *Zhonghua Yi Xue Yi Chuan Xue Za Zhi*, 20 (2): 135-137 (2003) (Abstract).

MedlinePlus [Internet]. Bethesda (MD): National Library of Medicine (US); Sep. 1, 2005]. "Danshen (*Salvia miltiorrhiza*)," [Updated Dec. 13, 2005]. Available from: <http://www.nlm.nih.gov/medlineplus/druginfo/natural/patient-danshen.html>.

Chandler et al., "Cardio Protective Activity of Synthetic Guggulsterone (E and Z—Isomers) in Isoproterenol Induced Myocardial Ischemia in Rats: a Comparative Study," *Indian J. Clin. Biochem.*, 18(2):71-79 (2003).

* cited by examiner

DIETARY SUPPLEMENTS FOR REDUCING CHOLESTEROL LEVELS

BACKGROUND OF THE DISCLOSURE

Field of the Disclosure

The disclosure is generally directed to methods and compositions for reducing blood cholesterol levels, and more particularly to dietary supplements for reducing blood cholesterol levels.

Brief Description of Related Technology

Coronary heart disease is the leading cause of death in the United States. Stroke is the third leading cause of death. These two manifestations of cardiovascular disease cause nearly 40 percent of all deaths in the United States (Anderson et al., "National Vital Statistics Reports, Deaths: Leading Causes for 2002," CDC, 53(17):1-92 (2005)).

Cardiovascular disease is caused by atherosclerosis in the blood vessels and arteries that supply the heart. Atherosclerosis is a process involving the gradual buildup of plaques (typically, over decades) on the inner linings of blood vessels and arteries. Over time, the plaques can occlude the blood vessels and arteries, causing ischemia (injury caused by insufficient blood flow and reduced oxygen to tissues) and/or infarction (cell death caused by ischemia). Plaques can also become unstable, rupture, and promote a thrombus (blood clot) that occludes a coronary artery. A severe plaque rupture in the coronary vasculature can lead to myocardial infarction (or heart attack).

Stroke is caused when pieces of plaque travel through the bloodstream and occlude an artery in the brain. Stroke can occur suddenly with immediate maximum neurologic deficit (loss of brain function).

Elevated blood cholesterol levels (total and LDL cholesterol levels) are considered risk factors for cardiovascular disease. In adults, total cholesterol levels of 240 mg/dL or higher are considered high risk, and levels from 200 to 239 mg/dL are considered borderline-high risk. About 99,900,000 of American adults have total cholesterol levels above 200 mg/dl, and about 34,500,000 have total cholesterol levels of 240 mg/dl or more (American Heart Association, Learn and Live, "High Blood Cholesterol and Other Lipids—Statistics" (2004)).

Other risk factors for cardiovascular disease include high blood pressure (140/90 mm Hg or higher), tobacco use, diabetes mellitus, overweight (body mass index of 25.0 to less than 30.0) and obesity (BMI of 30.0 or greater), physical inactivity (guidelines suggest at least 30 minutes of moderate exercise five times per week or at least 20 minutes of vigorous exercise three times per week), gender (males are at greater risk of developing cardiovascular disease), increasing age (55 years and older for men and 65 years or older for women), family history of early heart disease (having a mother or sister who has been diagnosed with heart disease before age 65, or a father or brother diagnosed before age 55) or family history of stroke. When one or more risks factors are identified in an individual, the risk of heart attack or stroke typically increases significantly.

Phytosterols are lipids having chemical structures similar to cholesterol, which are present in all plants including but not limited to vegetables, fruits, and grains, particularly in nuts, seeds, and plant oils. Phytosterols inhibit intestinal cholesterol absorption, thereby lowering plasma total and low-density lipoprotein (LDL) cholesterol levels. Daily consumption of about one to two grams of phytosterols reduces the risk for cardiovascular disease by about 25 to about 28% without causing any adverse effects. Twice per day consumption of about 0.40 grams of phytosterols or about 0.65 grams of phytosterol esters has also been shown to lower total cholesterol levels and LDL cholesterol levels by up to 10%.

Soluble fiber is found in certain foods including oats, peas, beans, certain fruits, and psyllium. Soluble fiber has been scientifically proven to reduce blood cholesterol levels, which may help reduce the risk of coronary vascular disease. Consumption of 10.2 grams psyllium per day over an eight week period lowered serum total cholesterol by 4% (p<0.0001) and LDL cholesterol by 7% (p<0.0001) relative to placebo in subjects already consuming a low-fat diet, with no effect on serum HDL or triacylglycerol concentrations. Similarly, consumption of 15 grams of beta-glucan daily over a three week period by individuals having initial total cholesterol levels exceeding 260 mg/dL reduced total cholesterol by about 19% and LDL cholesterol by about 23%. In another study, individuals having total cholesterol levels ranging from 210 to 326 mg/dL consumed 3.5 g of beta-glucan daily and experienced a 5.4% reduction, in total cholesterol after two weeks.

Guggul lipid has been long used to treat obesity and other weight related problems, and offers considerable benefits in preventing and treating atherosclerotic vascular disease. The effects of the administration of 50 mg of guggul lipid or placebo capsules twice daily for 24 weeks were compared as adjuncts to a fruit- and vegetable-enriched diet in the management of 61 patients with high cholesterol levels (31 patients were in the guggul lipid group and 30 were in the placebo group) in a randomized, double-blind fashion. Guggul lipid decreased the total cholesterol level by 11.7%, the low density lipoprotein cholesterol (LDL) by 12.5%, triglycerides by 12.0%, and the total cholesterol/high density lipoprotein (HDL) cholesterol ratio by 11.1% from the post-diet levels, whereas the levels were unchanged in the placebo group. The lipid peroxides, indicating oxidative stress, declined 33.3% in the guggul lipid group without any decrease in the placebo group. The combined effect of diet and guggul lipid at 36 weeks was as great as the reported lipid-lowering effect of many modern drugs. Guggul lipid contains ketonic steroid compounds known as guggulsterones, which have been shown to provide the lipid-lowering actions.

Policosanol is a mixture of long-chain primary aliphatic alcohols derived from the waxes of plants such as sugar cane (Saccharum officinarium) and yarns (e.g., Dioscorea opposita). Such long-chain primary aliphatic alcohols are also found in beeswax. There are a number of studies suggesting that policosanol consumption can lower cholesterol, inhibit experimentally induced atherosclerotic lesions of cerebral ischemia, help prevent the peroxidation of lipoproteins, and inhibit platelet aggregation. In one study, patients with LDL-cholesterol levels exceeding 160 mg/dl were randomized in double-blind fashion to receive policosanol (10 mg/day), lovastatin (20 mg/day), or simvastatin (10 mg/day). After eight weeks, policosanol reduced LDL-cholesterol levels by about 24%, lovastatin reduced LDL-cholesterol levels by about 22%, and simvastatin reduced LDL-cholesterol levels by about 15%. Additionally, HDL-cholesterol levels increased significantly in the policosanol group but not in the groups receiving statin drugs.

Dietary supplementation with salts of glucaric acid such as D-glucarate reduced serum cholesterol in rats (Walaszek et al., Nutr. Res., 16: 673-681 (1996)). Both calcium and potassium salts of D-glucarate were effective in lowering total cholesterol levels by about 13-15% and LDL cholesterol levels by about 30-35%. Notably, potassium hydrogen D-glucarate was effective in lowering both VLDL cholesterol and total triglycerides, but calcium D-glucarate did not demonstrate similar effects.

Anthocyanins are pigment compounds found in all plants, which have antioxidant and anti-inflammatory properties. Anthocyanins are generally considered to be flavonoids, and more specifically to be derivatives of 2-phenylo-benzo-g pyren. Hypertension, atherosclerosis, and diabetes can reduce the flexibility of arterial walls, which can contribute to poor blood flow and plaque formation. Rat aortas exposed to anthocyanin-enriched blueberry extract in vitro exhibited relaxation (Zaragoza et al., *Arch. Farmacol. Toxicol.*, 11:183-188 (1985)). Other studies suggest that anthocyanins provide cardio-protective benefits including reducing platelet aggregation.

Coenzyme Q10 (CoQ10) is essential for human life. It catalyzes the formation and utilization of energy in every human cell. Some people do not manufacture enough CoQ 10, especially as they grow older. Research has shown that COQ10 deficiency is a major cause of cardiomyopathy, and congestive heart failure, and that these diseases can often be cured by CoQ 10 supplementation. Coenzyme Q 10 is commonly added to multivitamin preparations.

Phytoestrogens such as resveratrol have also been shown to have cardioprotective effects. Resveratrol is a polyphenolic compound found in the skin of red grapes, which is a powerful phytoestrogen, cardioprotectant, and anti-oxidant. Other sources of resveratrol include peanuts, mulberries, and the dried roots and stems of *Polygonum cuspidatum*. Resveratrol has been shown to induce leukotriene production in human neutrophils. Leukotrienes are powerful mediators of inflammatory reactions and are thought to be involved in the cellular processes that contribute to atherosclerosis (Pace-Asciak et al., *Clin. Chim. Acta.*, 235:207-219 (1995)). Administration of resveratrol to rats which were fed a high cholesterol diet inhibited cholesterol and triglyceride liver deposition, lowered serum triglyceride and low-density lipoprotein (LDL) cholesterol levels, and reduced the ratio of total cholesterol to high-density lipoprotein (HDL) cholesterol (Arichi et al., *Chem. Pharm. Bull.*, 30:1766-1770 (1982)).

Chromium helps to prevent the buildup of plaque in arteries by lowering harmful low-density lipoprotein (LDL) cholesterol and increasing beneficial high-density lipoprotein (HDL) cholesterol. Despite its benefits, chromium is difficult for the body to absorb and retain. Compounding the problem, the average American diet is low in chromium.

Pantethine is the disulfide dimer of pantetheine, the 4'-phosphate derivative of which is an intermediate in the conversion of the B vitamin pantothenic acid to coenzyme A. Large amounts of pantethine have been found to have lipid-lowering effects. Pantethine has been found to decrease serum levels of total cholesterol, low-density lipoprotein cholesterol (LDL), and triglycerides.

Consumption of artichoke leaf extract (ALE) has also been shown to lower cholesterol levels. Also, the Chinese herb, *Salvia miltiorrhiza* (also known as dansheng), has been traditionally associated and recommended for heart conditions.

The progression of atherosclerosis and the onset of cardiovascular disease can be slowed or even prevented by reducing total and LDL cholesterol levels. Existing pharmaceuticals are capable of treating elevated cholesterol levels, but the majority cause significant side-effects, such as liver problems. Thus, a dietary supplement capable of reducing blood cholesterol levels without causing significant side-effects would represent a significant advance for treatment of cardiovascular disease.

DETAILED DESCRIPTION

The disclosure provides dietary supplements for reducing blood cholesterol, particularly total cholesterol and LDL cholesterol levels, while preferably maintaining and/or increasing HDL cholesterol levels. The disclosure further provides methods of treating individuals having high cholesterol levels and/or at risk of developing high cholesterol levels. Additionally, the disclosure provides methods of treating and/or preventing the onset of cardiovascular disease in individuals having one or more risk factors for developing such disease.

The dietary supplements typically comprise at least one phytosterol source, at least one soluble fiber source, at least one guggulsterone source, and at least one policosanol source. In another aspect, a method for reducing cholesterol levels comprises administering a dietary supplement comprising at least one phytosterol source, at least one soluble fiber source, at least one guggulsterone source, and at least one policosanol source to an individual in need thereof. An individual in need of such treatment typically has one or more of the risk factors for developing cardiovascular disease, although other individuals may benefit from taking the disclosed dietary supplement compositions, too.

As used herein, the term "dietary supplement" refers to a suggested serving (or dosage) of the disclosed cholesterol-reducing supplement composition. Typically, the suggested serving is consumed once per day, but in some instances, the suggested serving is consumed two, three, or even more times per day (with or without food). The dietary supplements can be formulated as pills, capsules, tablets, powders, liquids, or other forms consistent with oral and/or injectable administration. Administration can include administering the composition as part of foods or beverages including but not limited to lozenges, gums, bars, shakes, drinks, and other processed or prepared foods. Most frequently, the dietary supplements are dissolved in water to provide a daily serving.

The dietary supplements typically contain phytosterols in an amount sufficient to reduce cholesterol levels when combined with other active ingredients. The dietary supplements typically include contain at least about 250 milligrams (mgs), about 500 mgs to about 4500 mgs, and/or about 1000 mgs to about 2500 mgs, frequently about 1500 mgs phytosterols per serving. Phytosterols include but are not limited to sitosterol, campesterol, sitostanol, brassicasterol, and stigmasterol. The phytosterol source can be any natural source of phytosterols including but not limited to vegetable oil, soybean oil, shea nut oil, rice bran oil, extracts and extract products isolated therefrom, and mixtures thereof. CARDIOAID-L™ phytosterols and CARDIOAID-M™ phytosterols are suitable commercially available sources of phytosterols (Archer Daniels Midland Co., IL). CARDIOAID-M™ phytosterols are at least 95 weight percent (wt. %) phytosterols. COROWISE™ phytosterols are an additional suitable commercially available source of phytosterols (Cargill, Incorporated, Minneapolis, Minn.).

The dietary supplements typically contain soluble fiber in an amount sufficient to reduce cholesterol levels when combined with other active ingredients. The dietary supplements typically include contain at least about 200 milligrams (mgs), about 200 mgs to about 1000 mgs, and/or about 350 mgs to about 750 mgs of soluble fiber per serving. Suitable soluble fiber sources include oats, peas, beans, certain fruits, extracts and extract products isolated therefrom, and mixtures thereof. Psyllium husks are also a suitable source of soluble fiber; approximately 35 weight percent (wt. %) of psyllium husks are soluble fiber. Oat bran concentrates are also suitable sources of soluble fiber. A representative oat bran concentrate is OATVANTAGE™ oat concentrate (Nurture, Inc., Missoula, Mont.); approximately 54 wt. % of OATVANTAGE™ oat concentrate is beta glucan, a soluble fiber. Of course, other soluble fiber sources containing beta-glucan can also be used. In a preferred embodiment, the dietary supplements comprise psyllium husks and an oat bran concentrate.

The dietary supplements typically contain guggulsterones in an amount sufficient to reduce cholesterol levels when combined with other active ingredients. The dietary supplements typically contain at least about 2.5 mgs, about 2.5 mgs to about 15 mgs, and/or about 5 mgs to about 10 mgs of guggulsterones (E guggulsterone and/or Z guggulsterone) per serving, although amounts up to about 25 mgs per serving may also be used. A suitable source of guggulsterones is guggul lipid. Gugul lipid is a powdered extract product of the oleogum resin of *Commiphora mukul* plants, which is typically purified and standardized to contain a minimum of 2.5 wt. % guggulsterones. Thus, the dietary supplements typically contain at least about 100 mgs, about 100 mgs to about 600 mgs, and/or about 200 mgs to about 400 mgs of guggul lipid.

The dietary supplements typically contain policosanol in an amount sufficient to reduce cholesterol levels when combined with other active ingredients. The dietary supplements typically contain at least about 5 mgs, about 5 mgs to about 50 mgs, and/or about 10 mgs to about 25 mgs of policosanol per serving. Policosanol is typically a mixture of higher aliphatic alcohols including 1-octacosanol, 1-dotriacontanol, 1-triacontanol, 1-tetracosanol, 1-tetratriacontanol, 1-hexacosanol, 1-heptacosanol, and/or 1-nonacosanol. For purposes of this disclosure, the term "policosanol" refers to any combination of the aforementioned higher aliphatic alcohols, and in some embodiments, refers to a single higher aliphatic alcohol compond.

In one embodiment, the dietary supplements further comprise a salt of glucaric acid. When a glucarate salt is included, the dietary supplements typically contain at least about 50 mgs, about 50 mgs to about 350 mgs, and/or about 100 mgs to about 300 mgs of the glucarate salt per serving. The glucarate salt can be a disodium salt, a sodium hydrogen salt, a dipotassium salt, a potassium hydrogen salt, a calcium salt, or any other suitable salt, or any mixture thereof. Most preferably, the glucarate salt is potassium hydrogen D-glucarate. A suitable source of potassium hydrogen D-glucarate is PREVENTIUM® potassium hydrogen glucarate (Applied Food Sciences, LLC, TX).

In a further embodiment, the dietary supplements further comprise an anthocyanin source. When an anthocyanin source is included, the dietary supplements typically contain at least about 20 mgs, about 20 mgs to about 250 mgs, and/or about 50 mgs to about 150 mgs of the anthocyanin source per serving. Typically, the anthocyanin source is a berry extract derived from blueberrys, strawberrys, cranberrys, bilberrys, elderberrys, raspberrys, or mixtures thereof. Wild, conventionally grown, and/or organic berries may be used in the preparation of the berry extract. A suitable anthocyanin source is OPTIBERRY® berry extract (InterHealth Nutraceuticals, Benicia, Calif.).

In yet another embodiment, the dietary supplements further comprise coenzyme Q10. When coenzyme Q10 is included, the dietary supplements typically contain at least about 20 mgs, about 20 mgs to about 200 mgs, and/or about 50 mgs to about 150 mgs of the coenzyme Q10 per serving.

In other embodiments, the dietary supplement also comprises at least one phytoestrogen source. When a phytoestrogen source is included, the dietary supplements typically contain at least about 5 mgs, about 5 mgs to about 25 mgs, and/or about 7.5 mgs to about 15 mgs of phytoestrogens per serving. The phytoestrogen source may be any source of phytoestrogens, but preferably comprises a resveratrol source. The resveratrol source can be derived from the skin of red grapes, peanuts, mulberries, the dried roots and stems of *Polygonum cuspidatum*, or combinations thereof. One suitable source of resveratrol is a natural plant extract derived from *Polygonum cuspidatum* sold under the PROTYKIN® tradename (InterHealth Nutraceuticals, Benicia, Calif.). PROTYKIN® extract contains about 50 wt. % transveratrol.

The dietary supplements can also further comprise a chromium source. When a chromium source (or chromium complex) is included, the dietary supplements typically contain at least about 25 micrograms (mcgs), about 25 mcgs to about 200 mcgs, and/or about 50 mcgs to about 150 mcgs of the chromium source per serving. The chromium source can be any chromium complex including but not limited to chromium chloride and chromium picolinate, but preferably is niacin-bound chromium (or chromium polynicotinate), which is a form of chromium that is generally more readily absorbable than other forms of chromium. CHROMEMATE® chromium polynicotinate (InterHealth Nutraceuticals, Benicia, Calif.) is an exemplary niacin-bound chromium.

In other embodiments, the dietary supplements can also further comprise pantethine, or less preferably pantothenic acid or other derivatives thereof (such as calcium pantothenate). When pantethine is included, the dietary supplements typically contain at least about 50 mgs, about 50 mgs to about 1000 mgs, and/or about 100 mgs to about 500 mgs of panthethine per serving. A greater amount of pantothenic acid (or other derivatives of pantothenic acid) is usually required if pantothenic acid is used in lieu of pantethine (as pantethine is located nearer to coenzyme A than pantothenic acid in the biosynthetic pathway of coenzyme A). Thus, suitable equivalent dosages of pantothenic acid and/or other derivatives thereof (not including pantethine) can be readily determined by one of ordinary skill in the art. PANTESIN® HF-55 pantethine (Daiichi Fine Chemical Company, Co., Japan; Tomen America, Inc., NY) is an exemplary pantethine source, which contains about 55 wt. % pantethine.

Artichoke leaf extract (ALE) can also be included in the dietary supplements. Typically, the ALE is prepared from the leaves of the artichoke plant. Flavonoids and caffeolyquinic acids are believed to be the active components of ALE. Specific active compounds include chlorogenic acid, cyanarin, luteolin, scolymoside, and cynaroside. When ALE is included, the dietary supplements typically contain at least about 25 mgs, about 25 mgs to about 400 mgs, and/or about 50 mgs to about 200 mgs of ALE per serving.

In other embodiments, the dietary supplements can include an extract or extract product of *Salvia miltiorrhiza* (the Chinese herb also known as dansheng). When dansheng extract is included, the dietary supplements typically contain at least about 50 mgs, about 50 mgs to about 250 mgs, and/or about 100 mgs to about 200 mgs of dansheng extract per serving. MSV-60® extract (Technical Sourcing International, Inc., MT) is an exemplary powdered source of dansheng extract; the extract product contains magnesium salvianolate B at about 60 wt. %. Thus, stated alternatively, the dietary supplement can include at least about 30 mgs, about 30 mgs to about 150 mgs, and/or about 60 mgs to about 120 mgs of magnesium salvianolate B per serving.

Various natural or artificial flavoring components may also be included in the dietary supplement compositions to mask or block the extant flavors of various of the other components or otherwise flavor the dietary supplements. Conventional food supplement additives may also be included. Representative food supplement additives include but are not limited to sugar substitutes, maltodextrin, fructose, citric acid, and emulsifiers such as lecithin.

The disclosed compositions and methods for reducing cholesterol can be better understood in light of the following examples. However, the foregoing description and the following examples are merely illustrative, and therefore no unnecessary limitations should be understood therefrom as numerous modifications and variations are expected to occur to those skilled in the art.

Example 1

An essentially dry powder constituting a dietary supplement, comprising the following ingredients in the proportions indicated: a first phytosterol source (2500 mgs) (CARDIOAID-L™ phytosterols), a first soluble fiber source (540 mgs) (OATVANTAGE™ oat concentrate), a salt of glucaric acid (200 mgs) (PREVENTIUM® potassium hydrogen glucarate), a guggulsterone source (guggul lipid) (350 mgs), a second soluble fiber source (1185 mgs) (psyllium husks), citric acid (300 mgs), a second phytosterol source (1250 mgs) (COROWISE™ phytosterols), lecithin (70 mgs), dansheng extract (150 mgs) (MSV-60® extract), a phytoestrogen source (25 mgs) (PROTYKIN® extract), a pantothenic acid derivative (360 mgs) (PANTESIN® HF-55 pantethine), a policosinol source (20 mgs), artichoke leaf extract (100 mgs), oligofructose based sugar substitute (1700 mgs), flavoring components (1300 mgs), natural flavorings (800 mgs), an anthocyanin source (100 mgs) (OPTIBERRY® berry extract), a chromium source (10 mcgs) (CHROMEMATE® chromium polynicotinate), and coenzyme Q 10 (50 mgs).

Using a conventional plow blender set for continuous mixing, the first phytosterols are introduced into the mixing chamber with the blender in operation. Oat bran concentrate is then gradually added, followed by potassium hydrogen D-glucarate and guggul lipid; psyllium husks; citric acid; the second phytosterols; and, then lecithin. The composition was blended for approximately 8 minutes, followed by addition of dansheng extract, trans-resveratrol, pantethine, polycosinol, and artichoke extract; oligofructose based sugar substitute; other flavoring components; natural flavorings; chromium polynicotinate, and coenzyme Q 10. The composition was blended for approximately 8 additional minutes to produce a uniformly-mixed dietary supplement.

Example 2

The lipid-lowering properties of the dietary supplement of Example 1 were investigated using a double blind placebo-controlled clinical study. The study included two active phases and one placebo phase. Two groups of subjects were studied; one group was taking statin drugs and the other was not taking any cholesterol-lowering drugs, but was hypercholesterolemic. Safety was investigated with a battery of tests including blood chemistry, coagulation, hematology, blood pressure and weight.

The dietary supplement taken daily (11 g) was significantly more effective in lowering lipids than the placebo. Combining both groups the product lowered total cholesterol by about 6.8% ($p<0.001$), decreased LDL cholesterol by about 8.3% ($p<0.001$), and lowered the total cholesterol/HDL ratio (corresponding to heart disease risk) by about 9.4% ($p<0.001$). Triglycerides were also improved and declined by about 11.6%, but the change was not significant. An additional benefit was the lowering of glucose levels by about 4.8% ($p<0.001$). Further, HDL was increased almost 4% in the group not taking cholesterol-lowering drugs.

With respect to cholesterol levels, 67% of all subjects experienced a decrease, and seven of the 34 subjects (21%) having elevated cholesterol levels (>200 mg/dL) dropped out the category of elevated cholesterol. Moreover, five of the eight subjects with normal cholesterol levels (<200 mg/dL) experienced a decline. Overall, 70% of the subjects had a decrease in LDL cholesterol levels, and 11 of the 34 subjects (34%) having elevated LDL cholesterol levels (>130 mg/dL) were removed from the elevated LDL category. Similarly, 70% of subjects having HDL levels <35 mg/dL (which is considered a risk) experienced an increase in HDL levels, and four of the nine individuals (44%) were removed from the elevated risk area. Of the nine subjects having elevated triglycerides (>225 mg/dL), six (67%) were no longer in the high-risk category. Of the 23 subjects having an elevated cholesterol/HDL ratio (>5), seven (30%) were removed from elevated risk. Moreover, over 72% of all subjects had a reduction in the risk factor ratio (total cholesterol/HDL).

Furthermore, over 34% of all subjects experienced a decline in diastolic blood pressure and over 32% had a decrease in systolic blood pressure. With respect to homocysteine, an emerging risk factor for heart disease, 65% of all subjects had a decrease, and 44% of all subjects had a decrease for hs-CRP, although there were no significant changes. Of the 21 subjects having elevated glucose levels (>100 mg/dL, i.e subjects were pre-diabetic), 33% were transferred into the lower risk category after supplementation.

Compared to the placebo in both groups separately, the product significantly lowered cholesterol, LDL, and the risk ratio, and glucose (glucose was only significantly reduced in the group not taking statins). The dietary supplement was shown be safe and effective for reducing cholesterol levels, and thus decreasing the risk of coronary vascular disease.

The foregoing description has been given for clearness of understanding only, and thus no unnecessary limitations should be understood therefrom, as modifications within the scope of the invention are expected to occur to those having ordinary skill in the art. Accordingly, only such limitations as appear in the appended claims should limit the scope of coverage for this patent.

What is claimed is:

1. A dietary supplement for reducing cholesterol comprising:
   at least one phytosterol source;
   at least one soluble fiber source;
   at least one guggulsterone source;
   at least one policosanol source;
   an extract of *Salvia miltiorrhiza*; and,
   an anthocyanin source.

2. The dietary supplement according to claim 1, wherein the phytosterol source comprises at least one of sitosterol, campesterol, sitostanol, brassicasterol, and stigmasterol.

3. The dietary supplement according to claim 1, wherein the dietary supplement includes at least about 250 milligrams (mgs) of phytosterols per suggested serving of dietary supplement.

4. The dietary supplement according to claim 1, wherein the soluble fiber source comprises at least one of psyllium husks and extract products derived from oats, peas, and beans.

5. The dietary supplement according to claim 1, wherein the dietary supplement includes at least about 200 mgs of soluble fiber per suggested serving of dietary supplement.

6. The dietary supplement according to claim 1, wherein the soluble fiber sources comprises beta-glucan.

7. The dietary supplement according to claim 1, wherein the guggulsterone source comprises guggul lipid.

8. The dietary supplement according to claim 1, wherein the dietary supplement includes at least about 2.5 mgs of guggulsterones per suggested serving of dietary supplement.

9. The dietary supplement according to claim 1, wherein the policosanol comprises at least one of 1-octacosanol, 1-dotriacontanol, 1-triacontanol, 1-tetracosanol, 1-tetratriacontanol, 1-hexacosanol, 1-heptacosanol, and 1-nonacosanol.

10. The dietary supplement according to claim 1, wherein the dietary supplement includes at least about 5 mgs of policosanol per suggested serving of dietary supplement.

11. The dietary supplement according to claim 1, further comprising a salt of glucaric acid.

12. The dietary supplement according to claim 1, further comprising coenzyme Q10.

13. The dietary supplement according to claim 1, further comprising at least one phytoestrogen source.

14. The dietary supplement according to claim 1, further comprising a chromium source.

15. The dietary supplement according to claim 1, further comprising pantothenic acid or derivatives thereof.

16. The dietary supplement according to claim 15, wherein the panthothenic acid derivative is pantethine.

17. The dietary supplement according to claim 1, further comprising artichoke leaf extract.

18. A method for reducing cholesterol levels, comprising:
administering a dietary supplement comprising at least one phytosterol source, at least one soluble fiber source, at least one guggulsterone source, and at least one policosanol source to an individual in need thereof.

* * * * *